United States Patent [19]

Kirk et al.

[11] Patent Number: 5,276,170

[45] Date of Patent: Jan. 4, 1994

[54] AZIDO-SUBSTITUTED AROMATIC AMINO ACIDS

[75] Inventors: Kenneth L. Kirk, Bethesda, Md.; Robert Phillips, Athens, Ga.; David Hebel, Hertzlia, Israel

[73] Assignee: The United States of America as represented by the Department of Health and Human Services, Washington, D.C.

[21] Appl. No.: 821,056

[22] Filed: Jan. 16, 1992

[51] Int. Cl.$^5$ .......................................... C07C 247/16
[52] U.S. Cl. ......................................................... 552/8
[58] Field of Search ............................................ 552/8

[56] References Cited

PUBLICATIONS

Coudijzer, et al., *FEBS*, vol. 268(1), pp. 95-98 (1990).
Biochem. and Biophysical Research Comm., pp. 1123-1131, Aug. 15, 1985, vol. 130, No. 3, 1985, Cyrus R. Creveling et al.
Biochemistry 1985, vol. 24, 4694-4703, No. 17, Edith Wilson Miles et al.
Eur. J. Biochem., 117, 33-40 (1981), Toru Nagasawa et al.
Agr. Biol. Chem., 37 (4), 493-499 and 37 (3), 725-735, 1973, Hitoshi Enei et al.
J. Org. Chem., 1986, 51, 1175-1179, T. E. Walker et al.
Biotechnology and Bioengineering, vol. XXII, Suppl. 1, 127-161, (1980), Nobuyoshi Esaki et al.
Analytical Chemistry, vol. 59, No. 11, Jun. 1, 1987, pp. 1534-1538, Margaret E. Rice et al.

*Primary Examiner*—Marianne M. Cintins
*Assistant Examiner*—Kimberly J. Kestler
*Attorney, Agent, or Firm*—Birch, Stewart, Kolasch & Birch

[57] ABSTRACT

Azido-substituted aromatic amino acids represented by the following formula I are synthesized through the use of tyrosine phenol-lyase. The azido derivatives are suitable for use as photoaffinity labels and inhibitors;

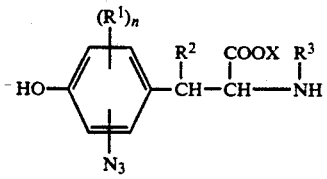

wherein $R^1$ represents a lower alkyl, a lower alkoxy, or an hydroxy group; $R^2$ and $R^3$ each independently represent a hydrogen or a lower alkyl group; X represents a hydrogen, a lower alkyl, an alkali metal, or an ammonium group; n is an integer of 0 to 3.

7 Claims, 1 Drawing Sheet

AZIDO-SUBSTITUTED AROMATIC AMINO ACIDS

BACKGROUND OF THE INVENTION

Field of the Invention

The present invention relates to azido-substituted aromatic amino acid derivatives having the azido group directly bonded to the aromatic ring, and their use as inhibitors and photoaffinity labels. The present invention also relates to an enzymatic process for synthesizing such azido-substituted derivatives.

Description of Related Arts

Azido-substituted aromatic derivatives in general are known in the prior art for use as inhibitors and photoaffinity labels. For instance, Eberle discloses that an activated aryl-azido-containing reagent can be introduced into the side chain of Arginine, Histine, Tyrosine or Tryptophan via a coupling reaction (see Eberle, A. N.,: Photoaffinity Labelling of Peptide Hormone Receptors, *J. Receptor Res.*, 1983, 3, 313-326; incorporated herein by reference). In one example, N-acetyl-3 (4-azidophenylazo)-tyrosine ethyl ester was prepared by coupling diazotized 4-azidoaniline with N-acetyltyrosine ethyl ester. A tyrosine containing analogue of bradykinn was also derivatized by coupling the tyrosine moiety with diazotized 4-azidoaniline in order to form a photoaffinity label. However, the presence of the affinity label at such a distal portion of the molecule is disadvantageous in that the label is more likely to covalently bond with a neighboring region rather than at the desired active site.

Similarly, the incorporation of p-azido- or p-nitro substituted phenylalanine into a peptide is another known photolabelling technique (see Escher, E. H. F.; Guillemette, G.: Photoaffinity Labelling of the Angiotensin II receptor, 3, Receptor Inactivation with photolabile Hormone Analogue, *J. Med. chem.*, 1979, 22, 1046-1050; incorporated herein by reference). Here the Tyr and/or Phe of a modified sequence of angiotensin II (Sar-Arg-Val-Tyr-Val-His-Pro-Phe) were replaced with 4-azido-Phe. The replacement of Tyr with azido-Phe produced analogues of weak affinity while substitution at Phe gave an active analogue. Thus, 4-azido-Phe is not an effective replacement for Tyr.

Another example of an aromatic amino acid having an azido group bonded directly to the aromatic ring is 6-azido-L-tryptophan (see Miles, E. W. ; Phillips, R. S.: Photoinactivation and Photoaffinity Labelling of Tryptophan Synthase $\alpha_2\beta_2$ Complex by the Product Analogue 6-Azido-L-tryptophan, Biochemistry, 1985, 24, 4694-4703; incorporated herein by reference). The azido derivatives were synthesized by converting a protected 6-azido-Trp via enzymatic cleavage of the ester ($\alpha$-chymotrypsin) and the amide (carboxypeptidase A) moieties.

However, the production of an azido-substituted tyrosine or dihydroxyphenylalanine (DOPA) having the azido group directly bonded to the aromatic ring is unknown in the prior art. This is probably due in part to the difficulty surrounding the synthesis of an azido-substituted aromatic amino acid derivative. Generally, the preparation of an aryl azide consists of diazotization of an aryl amine and subsequently treating with azide ion at 0° C. Alternatively, activated halides, such as 2,4-dinitrofluorobenzene, can be replaced by azide ion. But while some chemical manipulation of aryl azides is compatible with the reactivity of the azido group, the de novo chemical synthesis of azido amino acids from simple starting materials, such as 3-azidophenol, is problematic. The normal synthetic sequences require a combination of strong acid and/or strong basic conditions in order to remove the protecting ester and amide groups. These drastic hydrolytic conditions are incompatible with the azido group (see, for example, the typical azido incompatible deprotecting conditions used in scheme 10 of Creveling, C. R. and Kirk, K. L.: The effect of ring-fluorination on the Rate of O-Methylation of dihydroxyphenylanine (DOPA) by Catechol-O-Methyltransferase: Significance in the Development of $^{18}$F-Pet Scanning Agents, *Biochem Biophys. Res Commun.* 1985, (36, 1123-1131; incorporated herein by reference). Thus, a conventional chemical synthesis for azido-Tyr or DOPA would be possible only if exquisitely sensitive protecting groups could be utilized. However, the use of such protecting groups would substantially complicate the synthesis route.

SUMMARY OF THE INVENTION

It is an object of the present invention to provide new azido-substituted biogenic amino acid derivatives.

It is another object of the present invention to synthesize such azido-substituted derivatives via an enzymatic route.

It is a further object of the present invention to provide new inhibitors and photoaffinity labels for use in pharmacological and biochemical studies.

These and other objects are accomplished by compounds of the following formula I:

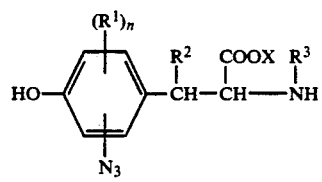

wherein $R^1$ represents a lower alkyl, a lower alkoxy, or an hydroxy group; $R^2$ and $R^3$ each independently represent a hydrogen or a lower alkyl group; X represents a hydrogen, a lower alkyl, an alkali metal, or an ammonium group; n is an integer of 0 to 3.

The invention also provides a process for synthesizing the compounds of formula I by reacting ammonium pyruvate or serine with the appropriate azido-substituted catechol or phenol derivative in the presence of tyrosine phenol-lyase.

The invention also provides for the use of the compounds of formula I as an inhibitor or photoaffinity label in pharmacological and biochemical applications and research.

DETAILED DESCRIPTION OF THE INVENTION

Figure 1:
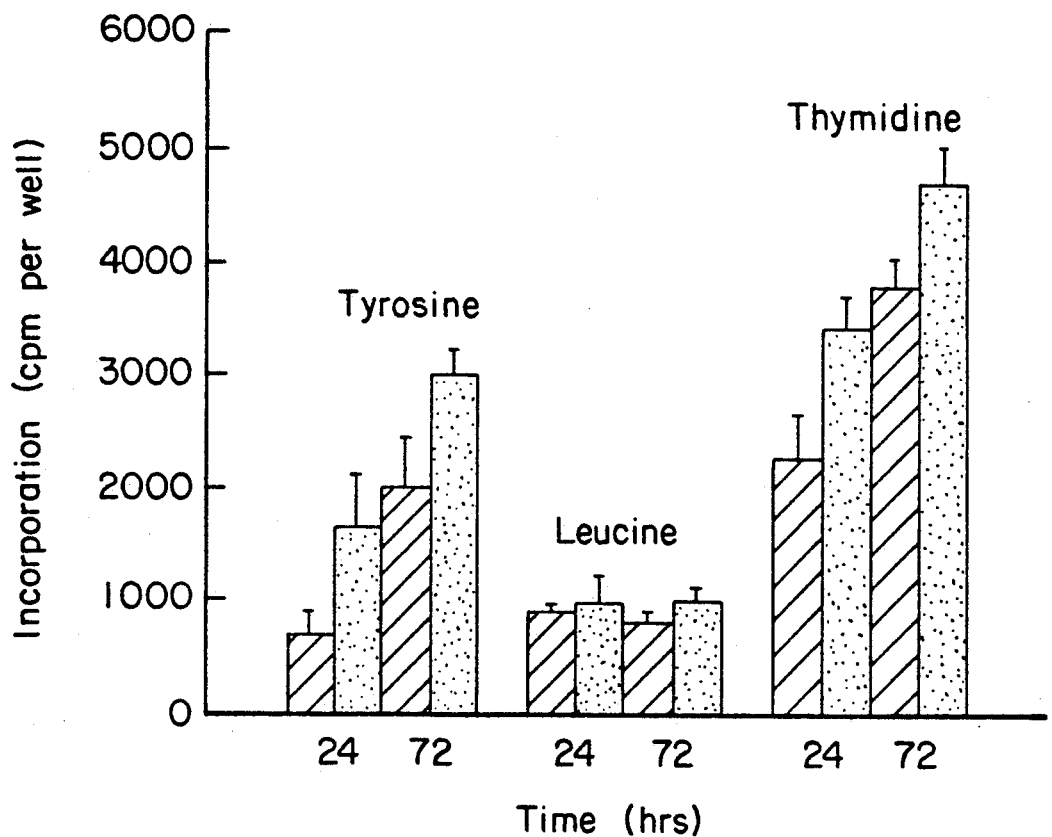
FIG. 1 shown the effect of 2-azidotyrosine on the incorporation of Tyrosine, Leucine and Thymidine into PC12 cell protein.

The present invention relates to azido-substituted tyrosine and DOPA derivatives as shown in formula I. Preferably, in formula I, $R^1$ represents a 1-6 carbon alkyl, a 1-6 carbon alkoxy, or a hydroxy group. $R^2$ and $R^3$ each independently represent a hydrogen or a 1-6 carbon alkyl. More preferably, $R^2$ and $R^3$ both represent a hydrogen. X preferably represents hydrogen, $Na^+$, $K^+$, $NH_4^+$ or a 1-6 carbon alkyl group. More preferably, X represents hydrogen. The azide moiety can be in the 2, 3, 5, or 6 position and is preferably in the 2 position. Additionally, the compounds according to formula I can be in the radio-labeled form, i.e. $^3H$, $^{14}C$, etc.

More preferably, the compounds of the present invention are represented by formula II:

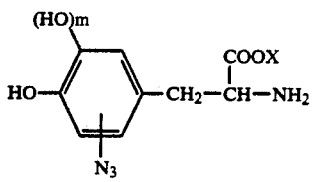

II wherein X is as defined in formula I and m is 0 or 1.

The compounds of the present invention, due to the presence of a chiral carbon, can be either "R" or "S" stereoisomers, but are preferably in the "S" configuration, as are naturally occurring tyrosine and DOPA.

Specific examples of the compounds of the present invention include the following:

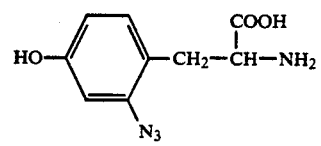

1

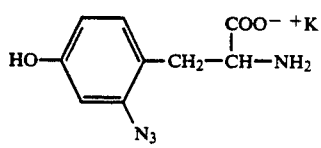

2

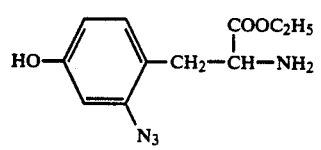

3

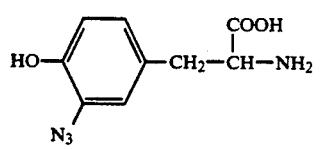

4

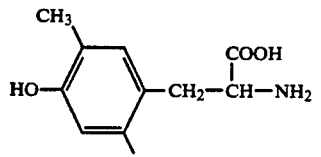

5

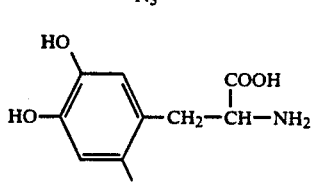

6

-continued

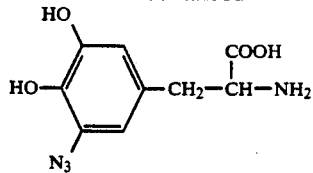

7

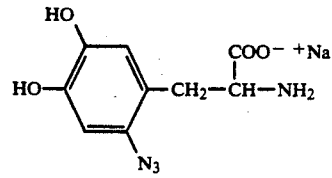

8

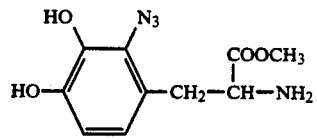

9

The azido-tyrosine and azido-DOPA derivatives of the present invention can be used to label the biogenic tyrosine and DOPA processing enzymes, such as tyrosinase and DOPA decarboxylase. After the label and the enzyme are preincubated and upon photolysis the azido moiety forms a covalent bond to the enzyme, via a nitrene intermediate; thereby causing irreversible inhibition of the enzyme. Without light activation, the azido group is substantially stable and will not covalently bond with the enzyme; hence the compounds of the present invention act as photoaffinity labels. Because the azido moiety is directly bonded to the aromatic ring, the compounds of the present invention serve not only to identify the presence of a particular enzyme, but also to study and elucidate the active sites of enzymes. The compounds of the present invention can be used according to any known prior art photoaffinity labeling technique, including radioassay, spectral absorption measurement, chromatographic separation, etc. Any of the tyrosine or DOPA processing enzymes can be labeled by the compounds of the present invention.

One of the enzymes that can be labeled by compounds of the present invention is tyrosinase. Tyrosinase is a naturally occurring enzyme that converts tyrosine into DOPA. The over production of tyrosinase is one effect of malignant melanomas. Indeed, malignant melanoma is one of only a few tumors for which there is such a chemical marker for metastases. In the past, the presence of large amounts of indolic melanin precursors in urine has been used as an indicator of melanoma metastases, and the quantitation of these substances in urine from melanoma patients has been used to monitor the progress of the disease. Also, the presence of DOPA and DOPA-derived products has been used to screen for melanoma metastases, although variations in the amount of normally produced products complicate the interpretation of these results.

More recently, a procedure for the determination of tyrosinase activity in patients with malignant melanoma has been described. Five out of seven sera from melanoma patients had tyrosinase activity, while no tyrosinase activity was found in seven sera from patients with other malignancies, or from controls having no malignancies. Following purification of protein fractions, stereospecific dopa oxidase activity was found in a protein that had many characteristics of soluble tyrosinase isolated from malignant melanoma cells. The assay used (determination of the amount of 5-S-L-cysteinyl-L-DOPA formed in the presence of D,L-DOPA and L-cysteine) was complicated by the non-enzymatic oxidation of DOPA (P,Agrup; R. Cartam, A. Wittbjer, H. Rorsman, and E. Rosengren, *Acta Derm, Venereal* (Stockh), 1989, 69, 120-124; incorporated herein by reference). Both the azido-tyrosine and azido-DOPA derivatives of the present invention can be used in such a melanoma testing procedure. It should be noted that azido-S-tyrosine is particularly preferred for use in such a procedure because of its unexpected ability to bind to tyrosinase while not being a substrate therefor. This ability avoids the complications caused by the usual conversion to the DOPA analogue and subsequent non-enzymatic oxidation.

In addition, the azido-DOPA derivatives of the present invention are useful for labelling DOPA-decarboxylase. Such labelling would allow for the determination of the active site of the enzyme as well as studies on the effect of DOPA decarboxylase inhibition.

The labelling of an enzyme using the photoaffinity labels of the present invention proceeds according to conventional techniques known to workers skilled in the art, such as shown in Phillips and Miles, cited above, which is expressly incorporated by reference, and comprises incubating an enzyme containing fraction from a sample with a compound of the present invention. The photoaffinity label of the present invention is generally used in amounts from about 0.5 to about 10 mmole per 1 ml of fraction, although amounts outside this range can be used. More preferably, about 1.0 to about 5.0 mmole of a compound of the present invention is incubated per 1 ml of fraction. The appropriate incubation temperature and time are readily determined by workers skilled in the art based upon the enzyme intended to be labelled. In general, the incubation temperature can range from 22°-52° C., but is usually around 37° C.

After incubation, photolysis is carried out by exposure to ultra violet light (i.e. 260-350nm), usually in a quartz cuvette. The time and intensity of the exposure are easily determined by workers skilled in the art.

The labelled enzymes are then separated and/or quantified as desired by conventional means, including the use of enzymes, a standardizing assay, high performance liquid chromatography and an autoradiogram. For convenience, it is preferred to use a radio-labelled form of the photoaffinity labels of the present invention as the labelling extent can be easily quantitated through the use of autoradiograms.

A particularly preferred use of the present invention combines the radiochemical assay of the present invention with an immunoprecipitation method. Monoclonal antibody probes have been used as markers to classify and detect melanoma-derived antigens (M. McEwan; P. G. Parsons: D. J. Moss; S. Burrows; D. Stenzel; C. J. Bishop; G. M. Strutton; *Pigment Cell Res.*, 1989, 2, 1-7, M. McEwan; P. G. Parsons; D. J. Moss; *J. Invest. Dermatol.*, 1988, 90, 515-519, To Tal; M. Elsinger; O. Shun-Ichiro; K. O. Lloyd; *Cancer Res.*, 1983, 43, 2773-2779; each incorporated herein by reference). By exploiting the availability of monoclonal antibodies for tyrosinase (M. McEwan et al., 1988, 1989) with photoaffinity labeling of serum-derived tyrosinase by the present invention, an increase in the specificity and sensitivity of detection of photoaffinity labelled tyrosinase can be achieved.

As normally applied, radioimmunoassays (RIA) are carried out by measuring inhibition of binding of radiolabelled antigen to specific antibody in unknown samples, and comparing the results with inhibition by standard solutions of unlabeled antigens. As such, RIA represents an indirect measurement. The antigen in the unknown sample, for example tyrosinase in sera of melanoma patients is radiolabelled by covalent attachment of $^3$H- or $^4$C-labelled 2-azido-S-tyrosine by photoaffinity labelling, as described above. Following photolabelling, using the procedure described above, quantitation of tyrosinase activity is accomplished by antibody precipitation using a previously characterized monoclonal antibody selective for human tyrosinase (McEwan et al, 1988).

Another use of the photoaffinity labels is to more accurately determine the tyrosinase activity in a serum sample using the assay described by Agrup et al, cited above. The procedure proceeds essentially as described by Agrup et al. After assaying according to Agrup et al, to determine the total amount of DOPA oxidation (enzymatic and nonenzymatic), the tyrosinase is then inhibited by photochemical attachment of the compounds of the present invention, followed by elution of the unreacted azido-derivatives. The Agrup et al assay is then re-applied in order to determine the amount of DOPA oxidation after tyrosinase inhibition. The so determined nonenzymatic oxidation is subtracted from the initial amount of total DOPA oxidation to give the amount of enzymatic oxidation. Such a method which utilizes the azido blocking effect of the present invention is more reliable than the conventional single assay method.

In addition to labelling enzymes, the azido-tyrosine derivatives of the present invention can also be utilized in labelling peptides.

Aryl azides have been introduced into intact peptides by coupling of suitably activated aryl-azido-containing reagents to amino, sulfhydryl, and carboxyl groups of side-chain Arg, His, Tyr, and Trp. A disadvantage of this prior art approach stems from the altered structures of the resulting molecules that can alter biological activity. Increased lipophilicity that accompanies such modifications also leads to increased non-specific binding. Replacement of Tyr and Phe in peptides with p-azidophenylanaline by de novo peptides synthesis has produced effective photoaffinity labels. Replacement of Tyr with 3-azido-S-tyrosine, rather than p-azidophenylalanine would be advantageous, since the replacement of Tyr with p-azidophenylalanine removes the phenolic OH group from the peptide, an alteration that could adversely affect receptor binding and selectivity. The following examples are presented to illustrate the use of the azido-tyrosine derivatives of the present invention by describing the use of 2-azido-S-tyrosine in the labelling of peptide receptor proteins.

Opioid peptides are an important class of Tyr-containing peptides, structural modifications of which have produced some of the most potent and receptor-selective ($\mu$, $\delta$ or $\kappa$) opioids. Using conventional solid-phase peptide synthesis procedures, several examples of 2-azido-L-tyrosine-containing opioid peptide analogues can be prepared. For example, dermorphin (Tyr-D-Ala-Phe-Gly-Tyr-Pro-Ser-NH$_2$) is a $\mu$A-specific opioid peptide, isolated from the frog skin of the genus *Phylmedusae*. Structural modifications of the active N-terminal tetrapeptide amide (Tyr-D-Ala-Phe-Gly-NH$_2$) have produced potent and receptor specific analogues. Thus, similar to the activity exhibited by the fluorotyrosine-containing analogue (Tyr(3-F)-D-Ala-Phe-Gly-NH$_2$. Tyr(2-N$_3$)-D-Ala-Phe-Gly-NH$_2$ shows high affinity for the $\mu$-receptor. Photochemical experiments can be conducted on tissue preincubated with 2-azido tyrosine in its [$^{14}$C]-labelled form, using the procedure described by Yeung (Yeung, C. W. T.: Photoaffinity Labelling of Opioid Receptor of Rat Brain Membranes with $^{125}$I(D-Ala$^2$, p-N$_3$-Phe$^4$-Met$^5$) Enkephalin, *Arch. Biochem. Biophys.*, 1987, 254, 81–91; incorporated herein by reference.

Similarly, the compounds of the present invention can be used to label angiotensinogen. The aspartyl protease renin cleaves the circulating protein angiotensinogen at the Leu-Val peptide bond to form angiotensin I (Asp-Arg-Val-Tyr-Ile-His-Pro-Phe-His-Leu). This is the biological precursor of the vasoconstrictive peptide angiotensin II (Asp-Arg-Val-Tyr-Ile-His-Pro-Phe). The potential for development of new strategies for the control of hypertension has prompted intense research on renin inhibitors and on the characterization of angiotensin receptors. Angiotensin receptors have been labelled previously using p-azido- or p-nitro-Phe in place of the Tyr$^4$ or Phe$^8$ residues. Angiotensin antagonists also have been developed, for example [p-azidobenzoyl 1,Ile$^8$]Angiotensin II Kwok, Y. C.: Moore, G. J.: Affinity Labelling of Angiotensin Receptors in the Rat Isolated Uterus with a Photolabile Antagonist, *Mol. Pharmacol.*, 1980, 18, 210–214; incorporated herein by reference. Using conventional solid-phase peptide synthesis, [2-N$_3$-Tyr$^4$]angiotensin II agonist can be prepared and used in photolabelling experiments as described in Kwok et al.

To this point, strategies to label receptors with a photolabile ligand derived from azido tryrosine have been discussed. A fundamentally different approach to the inhibition of binding has been developed wherein the receptor analogue serves as an antagonist to inhibit normal receptor-ligand binding. The human immunodeficiency virus (HIV) recognizes the CD4 cell surface antigen in a critical step in the establishment of infection. A benzylated derivative of a synthetic peptide (Thr-Tyr-Ile-Cys[Bzl]-Glu-Val-Glu-Asp-Gln-Lys-Glu-Glu) corresponding to residues 81–92 of the CD4 protein inhibits HIV-1-induced cell fusion and infection in vitro Lifson, J. D. : Hwang, K. M. ; Nara, P. L. ; Fraser, B.; Padgett, M.; Dunlop, N. M.; Eiden, L. E.: Synthetic CD4 Peptide Derivatives That Inhibit HIV Infection and Cytopathicity, *Science*, 1988, 241, 712–716; Nara, P. L.: Hwang, K. M.; Rasuch, D. M.; Lifson, J. D. ; Eiden, L. E.: CD4 Antigen-based Antireceptor Peptides Inhibit Infectivity of Human Immunodeficiency Virus in vitro at Multiple Stages of the Viral Life Cycle, *Proc. Natl. Acad. Sci. USA*, 1989, 86, 7139–7143; each incorporated herein by reference. Following the procedures described for the synthesis of this peptide, 2-N$_3$-Tyr can be incorporated in place of Tyr to produce a photolabile analogue of this receptor fragment; namely, Thr-(2-N$_3$-Tyr)-Ile-Cys[Bzl]-Glu-Val-Glu-Asp-Gln-Lys-Glu-Glu. Prior art procedures can be used to assay the effectiveness of this new analogue in blocking HIV viral infection in vitro. Through conventional photochemical labelling experiments the binding site on the surface of the HIV virus should be locatable.

Finally, the azido-substituted derivatives of the present invention can be advantageously incorporated into protein.

The biosynthetic incorporation of amino acid analogues into proteins has been an area of extensive research, and has produced much valuable information on the structure and function of proteins. The exact transfer of genetic information in the biosynthesis of proteins requires that peptide bonds be formed with minimal formation of incorrect sequences. Thus, in order to be incorporated into a protein, an analogue must survive the scrutiny of strict editing processes. These consist of the normal base pairing involved in codon-anti-codon interactions of aminoacyl-charged tRNA and mRNA according to the genetic code and the matching of individual amino acids with the correct tRNA. Thus, for efficient incorporation, an analogue must have close resemblance to its natural relative. There have been many skillful methods developed to maximize analogue incorporation, including such strategies as the use of auxotrophic microorganisms, enzyme induction, and, more recently, molecular biological cloning techniques. Analogue incorporation can be particularly useful if a biological tracer, for example $^{19}$F, or functional group is present in the analogue.

Incorporation of azido-substituted derivatives into protein using the strategies discussed above will have many applications. For example, tyrosine is present at the active site of many enzymes, such as $\beta$-galactosidase, and it should be possible to use the 2-N$_3$-Tyr-containing enzyme analogue to photochemically label the enzyme substrate with the enzyme active site. In addition, irradiation of 2-N$_3$-Tyr-containing proteins should lead to cross-linking within the protein backbone, giving information on three-dimensional structure of the protein.

The synthesis of the azido-substituted derivatives of the present invention is normally quite difficult as discussed above. However, the present inventors have discovered that azido-substituted derivatives of formula I and II can be synthesized via an enzymatic route. Specifically, the method according to the present invention comprises:

reacting a compound of the following formula III with ammonium pyruvate or serine in the presence of tyrosine phenol-lyase:

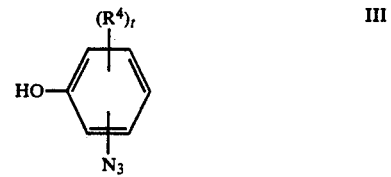

wherein R$^4$ is an hydroxy, a lower alkyl or a lower alkoxy group and t is 0 to 3, provided that neither N$_3$ nor R$^4$ occupies the position para to the hydroxy group.

The reaction can be carried out under the same general conditions as outlined by Nagasawa et al in *Eur. J. Biochem.*, 1981, 117, 33; incorporated herein by reference. The ratio of compounds of formula III to ammonium pyruvate or serine is generally in the range of 1:10 to 10:1, preferably 1:5 to 2:1, more preferably 1:3 to 1:1. The ammonium pyruvate or serine is normally used in stoichiometrically excessive amounts. The tyrosine phenol lyase is generally used in amounts of 0.1 to 10 units, preferably 1 to 5 units, more preferably about 3 units, per mmole of compound of formula III. The reaction is preferably carried out in a substantially neutral pH range (5.5 to 8.5) although other pH conditions can be used if desired. The reaction is normally conducted at room temperature although lower and higher temperatures are also operable. The resulting azido-substituted aromatic amino acid can then be esterified or placed into salt form by conventional methods. Alkyl substitution at the $R^2$ and $R^3$ positions can also be accomplished by conventional techniques, such as shown in Enei et al, *Agricultural & Biolog. Chem.*, 1972, 36, pg. 1869–1876, which is incorporated by reference. The radio-labelled form of the compounds present invention can be achieved by any conventional method, and include the use of radio-labelled reactants. For example, the use of a formula III compound that was synthesized from tritiated amino phenol or the use of $^{14}C$-serine or $^{14}C$-pyruvate (available from New England Nuclear) in the above described enzymatically catalyzed reaction will result in compounds of formula I in radio-labelled form.

In addition to providing a high yield of azido-substituted derivatives, the present method also yields an optically pure product containing only the "S" stereoisomer.

The compounds of formula III can be prepared by conventional prior art methods. For instance, 3-azidophenol can be prepared as disclosed in Ugi, I. et al; *Chem. Ber,* 1958, 91, 2330; incorporated herein by reference. An improved version of this method comprises carrying out the diazotization of 3-aminophenol in cold fluoroboric acid. Also the sodium azide should be added prior to the neutralization of the cold solution.

Similarly, 4-azidocatechol can be prepared by diazotization at 0° C. of 3,4 diacetoxyaniline (prepared according to Vasileve et al; *Zhi Obshch, Khim. ;* 1962, 2, 3088–3090 which is incorporated herein by reference) followed by treatment with $HN_3$ by the usual method. Mild basic hydrolysis (argon atmosphere) or, alternatively, in situ hydrolysis during incubation with tyrosinephenol lyase, will provide 4-azidocatechol.

3-Azidocatechol can be prepared from 3-nitrocatechol (Kampouris; *J. Chem. Soc. Perkin I,* 1972, 1088–1090 which is incorporated herein by reference) by acetylation to 3-nitrocatechol diacetate, reduction to 2,3-diacetoxyaniline, and diazotization and subsequent treatment with $HN_3$, as above. The intermediate 1-azido-3,4-diacetoxybenzene is converted to 3-azidocatechol by mild basic hydrolysis (argon atmosphere).

EXAMPLES

Example 1

A solution of 450 mg of m-azidophenol (3.33 mmol), 407 mg pyruvic acid, 1.8 mg of pyridoxal-5'-phosphate, 711 mg of ammonium acetate and 10 units of tyrosine phenol lyase in 74 ml of water was adjusted to pH 8 with dilute $NH_4OH$ and stored in the dark at room temperature for 4 d. The mixture was then acidified with dilute acetic acid and filtered through celite. The filtrate was extracted two times with 50 ml of ethyl acetate to remove unreacted azidophenol [200 mg (1.48 mmol) azidophenol was recovered]. An Amberlite IRA-118H column (1.5×10 cm) activated with 2N HCl and washed with water. The reaction mixture was passed through the column and eluted with 4% $NH_4OH$. The fractions that gave a positive ninhydrin reaction after spotting on silica gel plates were combined and lyophilized to give compound 1, 2-azido-L-tyrosine, as a white solid. Recrystallization from water gave 225 mg (1.01 mmol) of analytically pure 1, mp 200°–210° C. (decomp), $[\alpha]_D^{23}$ −8.62 (C=4, 1N HCl), IR (KBr) cm$^{-1}$ 3700–2600, 2110, 1605, UV ($H_2O$) $\lambda_{max}$ 219, 250, 290, ms (CI $NH_3$): 223 $(M+1)^+$, 179 $(M-COOH+1)^+$, 149 $[HOPhN_3(CH_3)]^+$, $^1H$ NMR ($D_2O$) 8 2.93 (1H, dd, $J_1$=14.5 Hz, $J_2$=8.2 Hz), 3.20 (1H, dd, $J_1$=14.5 Hz, $J_2$=5.3 Hz), 3.94 (1H, dd, $J_1$=8.2 Hz, $J_2$=5.3 Hz), 6.64 (1H, dd, $J_1$=8.3 Hz, $J_2$=2 Hz), 6.75 (1H, d, J=2 Hz), 7.12 (H, d, J=8.3 Hz).

Anal. calcd for $C_9H_{10}N_4O_3+1/3\ H_2O$, C 47.37, H 4.68, N 24.56; found, C 47.44, H, 4.80, N 24.48.

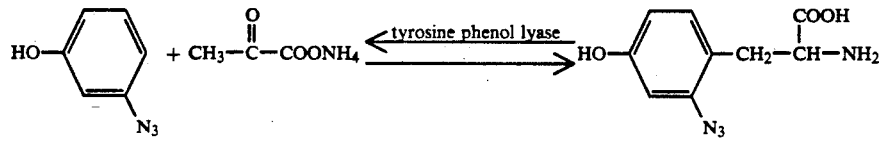

Example 2: The Effect On Cell Growth

Cell growth was estimated both visually and by the incorporation of [$^3H$]thymidine and [$^3H$]leucine over a period of 5 days in the presence and absence of nerve growth factor, 50 nanogm/well (NGF-7S was obtained from Boehringer Mannheim Biochemicals, Indianapolis, Ind.; labeled amino acids and thymidine were obtained from New England Nuclear, Boston, Mass.). On day one, compound 1 was added in concentrations ranging from 0.005 to 1.5 mM. Less than 10% inhibition in isotope-incorporation was observed between control and cultures over the five day period. Thus, compound 1, at a maximum concentration of 1.5 mM, did not significantly inhibit the growth of PC12 cells in the presence and absence of NGF over a period of 5 days.

Example 3: The Effect On Amino Acid Incorporation And On DNA Synthesis

The incorporation (2 $\mu$Ci/well) of [$^{14}CU$]tyrosine, [$^3H$]thymidine were measured in the presence and absence of 2-azidotyrosine (1.0 mM) over a period of 72 hours. PC12 cells were grown as monolayers in 150 cm$^2$ tissue culture flasks at 37° C. in 6% $CO_2$ in Dulbecco's modified Eagle's medium supplemented with 7% fetal bovine serum, 7% horse serum, and 100 $\mu$g streptomycin and 100 units of penicillin per ml. The cells were split after 3 days and aliquots (2 ml) transferred to 6 well culture plates. 2-Azidotyrosine (final concentration, 1 mM), [$^{14}CU$] tyrosine (2 $\mu$Ci/well), [$^3H$]leucine (2 $\mu$Ci/well), and [$^3H$]thymidine (2 $\mu$Ci/well) were added in 0.5 ml solutions in cell media. The final volume of each well was adjusted to 3.0 ml. The cultures were incubated in the dark at 37° C. in 6% $CO_2$ for 12, 24, 48 and 72 hrs. Cells were removed and transferred to conical tubes (10 ml), sedimented by centrifugation, and washed 3X with phosphate buffered saline, pH 7.2. The cell sediment was dissolved in 0.5 ml of a solution of 0.5N NAOH containing 1% SDS over a period of 30 min., neutralized with 0.5 ml 0.5N HCl, and the isotope content measured by scintillation spectrometry. The results are expressed at the mean±SEM for 3 wells for each set of conditions. As shown in FIG. 1, the incorporation of [$^{14}CU$]tyrosine was inhibited by approximately 58 to 38% (hatched bars) compared to untreated controls (solid bars) at 24 and 72 hrs. The incorporation [³H]leucine was not significantly different from control. The inhibition of [³H]thymidine incorporation was 34 and 24% at 24 and 72 hours respectively. Thus, the apparent incorporation of tyrosine into PC12-cellular protein was significantly reduced in the presence of 1 over a 72 hr period of linear growth. The incorporation of leucine was less than that of tyrosine and was not significantly inhibited by the presence of compound 1. These results indicate that 2-azidotyrosine can specifically inhibit the incorporation of tyrosine into protein in PC12 cells. In addition, the negligible inhibition of cell growth by compound 1 indicates that azido-tyrosine can replace tyr in protein-biosynthesis.

As expected, 2-azido-L-tyrosine is a good substrate for tyrosine phenol-lyase catalyzed hydrolytic cleavage to ammonium pyruvate and 3-azidophenol, with a $K_m$ of 1 mM and $V_{max}$ 18% that of L-tyrosine. Surprisingly, compound 1 is not hydroxylated by mushroom tyrosinase (sigma), since there was no detectable changes in its UV and visible absorption spectra upon extensive incubation. However, addition of compound 1 (0.1 mM) to tyrosinase solutions containing equimolar L-tyrosine resulted in much longer lag periods before oxidation proceeded, as determined by the production of dopaquinone at 480 nm. Thus, compound 1 is apparently able to bind strongly to mushroom tyrosinase.

From these results, it is seen that azido tyrosine mimics L-tyrosine in certain biochemical processes. The binding of compound 1 to mushroom tyrosinase, with no apparent oxidation, evidences the use of compound 1 as a photoaffinity label of this enzyme. Indeed azido-substituted analogues of dopamine and norepinephrine have the potential for providing similar active analogues that also could function as photoaffinity labels and irreversible inhibitors of key enzymes in the production and metabolism of neurotransmitters, as do the compounds of the present invention; although synthesis of such compounds is complicated by the sensitive nature of the azido group.

Example 4: Malignant Melanoma Detection

Protein fractions from sera collected from patients with malignant melanomas are purified essentially according to the procedure described by Agrup et al. (1989). The crude sera are treated with ammonium sulfate to a final concentration of 1M. After centrifugation at 30,000 g for 30 min., the supernatant is passed through a small phenyl-sepharose (Pharmacia, Sweden) column (50×5.5 mm) equilibrated with 1M (NH₄)₂SO₄ d20 mM KH₂PO₄_ pH 7.0. The column is washed with 2×5 mL of 1M ammonium sulfate (pH 7.0), the protein is eluted with 10 mL of 20 mM KH₂PO₄, pH 7.0. The eluant is passed through a Concanavalin-A-Sepharose (Pharmacia, Sweden) column (20×5.5 mm) in 4 mM KH₂PO₄. 1M KCl, pH 7.0. The column is washed with 4 mL of 4 mM KH₂PO₄. 1M KCl, pH 7.0, and 5 mL of 4 mM KH₂PO₄. pH 7.0, then eluted with 0.5M methyl-α-D-mannopyanoside, 4 mM KH₂PO₄. pH 7.0, in 1 mL fractions. 0.3 mL aliquots from these fractions are incubated at 37° C. with 0.7 mL solution of [¹⁴C]-labelled 2-azido-S-tyrosine. Photolysis is carried out at 22° C. in a quartz cuvette, using a Mineralight lamp Model UVGI. -25 at a distance of 5 cm. Following irradiation, proteins are separated by electrophoresis on SDS polyacrylamide slab gels. The autoradiograms are quantitated with a gel scanner. Results are compared with sera taken from normal volunteers and from patients with other malignancies.

What we claim is:

1. A compound represented by formula I:

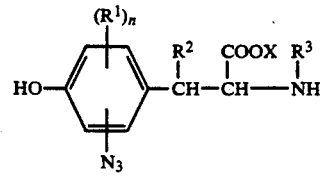

wherein $R^1$ represents a lower alkyl, a lower alkoxy, or an hydroxy group; $R^2$ and $R^3$ each independently represent a hydrogen or a lower alkyl group; X represents a hydrogen, a lower alkyl, an alkali metal, or an ammonium group; n is an integer of 0 to 3; and wherein the azido group is in the two position.

2. The compound according to claim 1, wherein n is 0.

3. The compound according to claim 1, wherein n is 1 and $R^1$ represents a hydroxy group at the 5 position.

4. The compound according to claim 1, wherein one of the carbon atoms is a ¹⁴C isotope.

5. The compound according to claim 1, wherein one of the hydrogen atoms is a ³H isotope.

6. The compound according to claim 1, wherein said compound is represented by formula II:

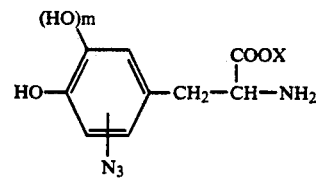

wherein X represents a hydrogen, a lower alkyl, an alkali metal, or an ammonium group and m is 0 or 1, and wherein the azido group is in the two position.

7. The compound according to claim 6, wherein said compound is:

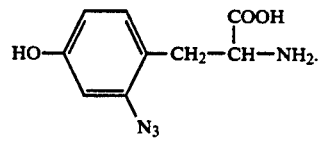

* * * * *